US00PP27699P3

(12) United States Plant Patent
Van Dijk

(10) Patent No.: US PP27,699 P3
(45) Date of Patent: Feb. 21, 2017

(54) ***ANTHURIUM* PLANT NAMED 'ANTHDATAM'**

(50) Latin Name: ***Anthurium andreanum* L.**
Varietal Denomination: ANTHDATAM

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 85 days.

(21) Appl. No.: 14/545,282

(22) Filed: Apr. 16, 2015

(65) Prior Publication Data

US 2016/0309638 P1 Oct. 20, 2016

(51) Int. Cl.
*A01H 5/02* (2006.01)

(52) U.S. Cl.
USPC ..... Plt./367

(58) Field of Classification Search
USPC ..... Plt./367, 369, 365
See application file for complete search history.

(56) References Cited

U.S. PATENT DOCUMENTS

PP12,115 P2 * 10/2001 van Dijk ..... Plt./367

OTHER PUBLICATIONS

New Plants and Flowers Jun. 3, 2014, Four new pot *anthuriums*, retrieved on Aug. 24, 2016, retrieved from the Internet at <http://www.newplantsandflowers.com/four-new-pot-anthuriums/> 2 pp.*
Pluto Plant Variety Database Aug. 10, 2016 for *Anthurium* 'Anthdatam', retrieved on Aug. 24, 2016, retrieved from the Internet at <http://www.upov.int/pluto/en/index.jsp> 1 page.*
Anthura *Anthurium*: Cut flower and pot plant culture, published Nov. 2014, pp. 1-3, 30, 47.
EU Community Plant Variety Rights Application No. 2012/2609, Application n°A201201557, filed Nov. 19, 2012, 7 pages.
EU Community Plant Variety Office Official Gazette, 1.2013, Feb. 15, 2013, Introductory 2 pages, pp. 1, 27, 44.
EU Community Plant Variety Rights Grant No. EU 38411, issued Jun. 16, 2014, 2 pages.
www.newplantandflowers.com/four-new-pot-anthuriums/, Jun. 3, 2014; 2 pages.

* cited by examiner

*Primary Examiner* — June Hwu
(74) *Attorney, Agent, or Firm* — Jondle & Associates, P.C.

(57) ABSTRACT

A new and distinct variety of *Anthurium* plant named 'ANTHDATAM' particularly characterized by having pink, very durable spathes that retain the original color for a long period of time, a red-purple spadix with an orangish tip, dark green, durable and glossy leaves, flowering continuously throughout the year, and a compact plant habit, is disclosed.

3 Drawing Sheets

Genus and species: *Anthurium andreanum* L.
Variety denomination: 'ANTHDATAM'.

BACKGROUND OF THE NEW PLANT

The present invention comprises a new and distinct variety of *Anthurium*, botanically known as *Anthurium andreanum* L., and hereinafter referred to by the variety name 'ANTHDATAM'. The new variety originated from a hybridization made in November 2006 in Bleiswijk, The Netherlands. The female parent is a purple *Anthurium* pot plant designated 'ANTHUCOEN' (U.S. Plant Pat. No. 22,630), and the male parent was a red *Anthurium* plant designated '10665-03' (unpatented).

A single plant was selected in August 2008 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Nov. 19, 2012, in China on Jan. 29, 2015, in Japan on Feb. 6, 2015 and in Mexico on Mar. 23, 2015. 'ANTHDATAM' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, pink, cordate spathe;
2) Red-purple spadix with orangish tip;
3) Compact plant habit; and
4) Shiny, dark green foliage.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 23-week old plant grown in a greenhouse in Bleiswijk, The Netherlands in March 2015.

DESCRIPTION OF THE NEW VARIETY

Figure 1:
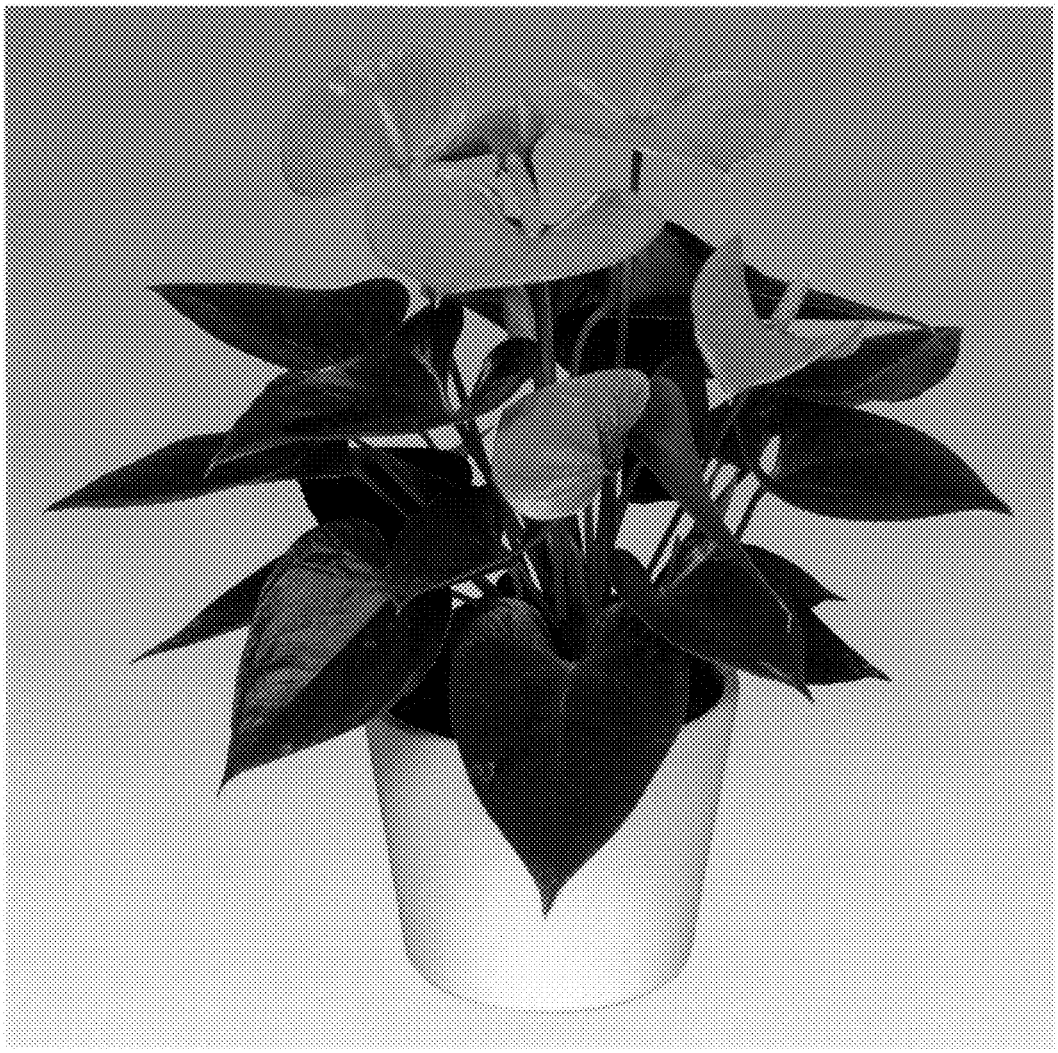
FIG. 1 shows the overall plant habit, including blooms, buds and foliage.
Figure 2:
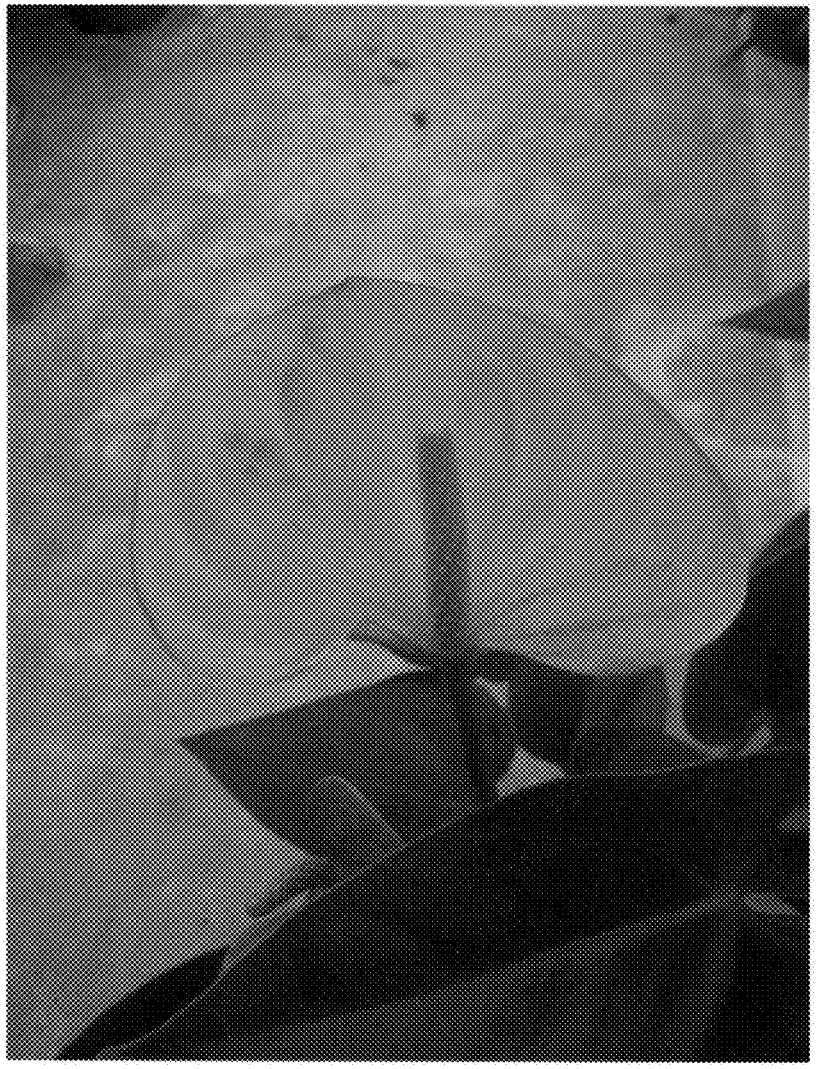
FIG. 2 shows a close-up of the mature spathe.
Figure 3:
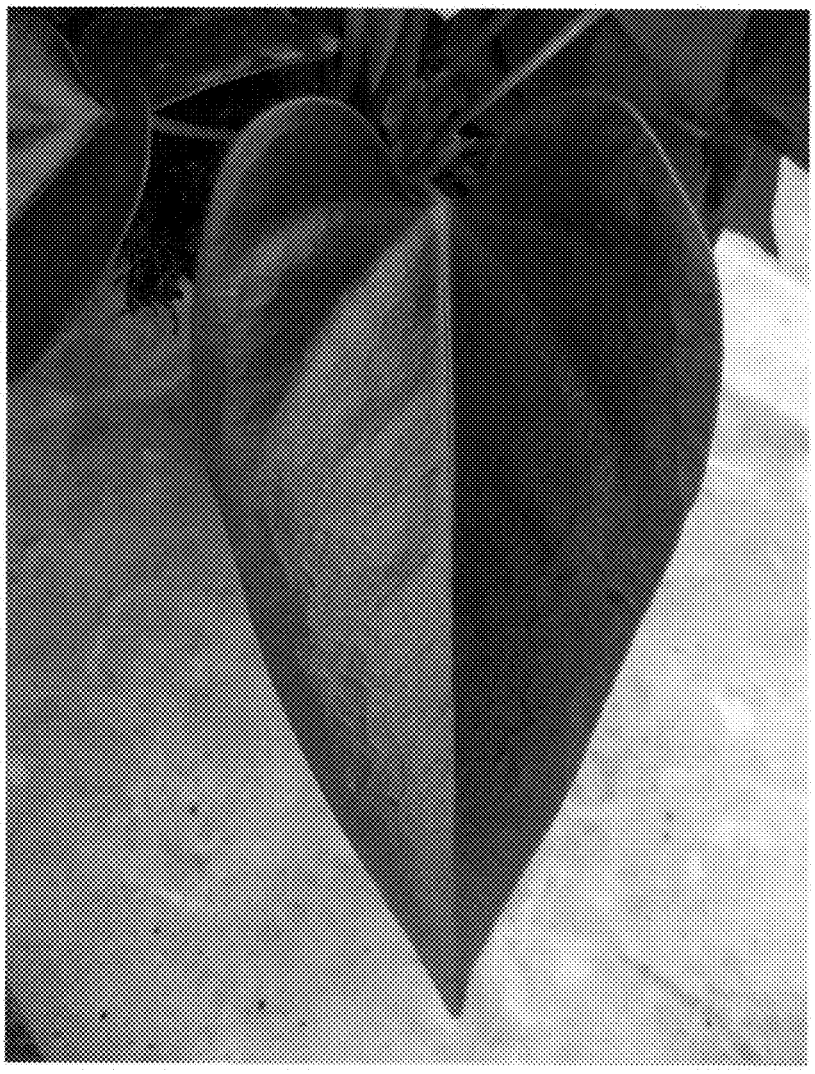
FIG. 3 shows the upper leaf blade surface.

The following detailed description sets forth the distinctive characteristics of 'ANTHDATAM'. The data which define these characteristics were collected from asexual reproductions carried out in Bleiswijk, The Netherlands. The plant history was taken on 23-week old plants which were planted from tissue culture in 12-centimeter pots and grown in a glass greenhouse between 19° C. and 24° C. Observations were made in March 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDATAM'.

Parentage:

*Female parent*.—*Anthurium* plant 'ANTHUCOEN' (U.S. Plant Pat. No. 22,630).

*Male parent*.—*Anthurium* plant '10665-03' (unpatented).

Plant:

*Propagation*.—Tissue culture.

*Root description*.—Fleshy white-cream colored roots with small hairy lateral roots having yellow-colored root tips.

*Time to produce a finished flowering plant*.—25 to 30 weeks for a 12 cm pot.

*Growth habit*.—Herbaceous perennial.

*Height* (*measured from soil, including inflorescence*).—22.0 cm to 26.0 cm.

*Width* (*measured from leaf tips*).—30.0 cm to 35.0 cm.

Leaves:

*Immature leaves*.—Length: 9.0 cm to 14.0 cm. Width: 6.0 cm to 8.0 cm. Color: Upper surface: RHS 147A. Lower surface: RHS 144A. Texture (both upper and lower surfaces): Shiny.

*Mature leaves*.—Length (fully expanded): 12.0 cm to 15.0 cm. Width: 7.0 cm to 9.0 cm. Shape: Ovate-cordate. Apex: Acuminate. Base: Cordate. Leaf blade angle with the petiole: Between 120 degrees and 140 degrees. Leaf margin: Entire. Color: Upper surface: RHS 139A. Lower surface: RHS 143A. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 143B. Lower surface: RHS 144B.

*Lobes*.—Arrangement: Leaf blade has two lobes extending past the petiole. The lobes are non-touching. Length of lobes of mature leaf blades: 1.0 cm to 2.0 cm. Width of lobes of mature leaf blades: 2.0 cm to 3.0 cm. Distance from petiole/leaf junction to highest point on lobes of mature leaf blades: 2.0 cm to 3.0 cm.

*Petiole*.—Cross-section: Round. Diameter: 0.2 cm to 0.3 cm. Length: 10.0 cm to 13.0 cm for a mature leaf size. Color: Mature leaf: RHS 143B. Immature leaf: RHS 144B. Cataphyll color surrounding the petiole: Outside: RHS 145A. Inside: RHS 145C.

*Geniculum*.—Length: 1.5 cm to 2.5 cm. Width: 0.25 cm to 0.35 cm. Color: RHS 143A.

Inflorescence:

*Arrangement*.—Single.

*Flowering habit* (*length of flowering season*).—Continuous.

*Number of inflorescences per plant*.—3 to 5.

*Fragrance*.—Absent.

*Longevity of inflorescence on plant*.—Over a year.

*Longevity of the flower as a cut flower*.—30 to 40 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 90 degrees and 110 degrees; the spathe stands on a wiry peduncle about 5.0 cm to 7.0 cm above the foliage.

*Lobe position*.—Free.

*Shape*.—Cordate.

*Apex*.—Mucronate.

*Base*.—Weakly cordate.

*Texture*.—Shiny and slightly blistered.

*Margin*.—Entire.

*Size*.—Height: 6.0 cm to 8.0 cm. Width: 6.0 cm to 8.0 cm.

*Color*.—Just fully open: Upper surface: RHS 52A. Lower surface: RHS 52B. Approximately 15 to 25 weeks after opening, veins in the spathe start greening to RHS 144A and 145C, which gives the veins a brown appearance.

Peduncle:

*Shape*.—Erect.

*Cross-section*.—Round.

*Length*.—18.0 cm to 22.0 cm.

*Diameter*.—0.2 cm to 0.3 cm.

*Color*.—RHS 144A.

Flowering time:

*General*.—One small rooted untreated tissue culture plant of 2.0 cm tall will flower after 4 to 6 months, depending on the season, and 4 to 6 blossoms will appear. More blossoms appear after some additional weeks so that a full flowering and commercial plant will have 5 to 7 pink spathes. Smaller blossoms may occur on less mature plants.

Spadix:

*Size*.—Length: 2.5 cm to 3.5 cm (depending on flower size). Width (at apex): 0.3 cm to 0.4 cm. Width (at base): 0.4 cm to 0.5 cm.

*Shape*.—Columnar.

*Angle from spadix tip to peduncle*.—160-180 degrees (spadix is almost in one line with peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 39B. Mature: RHS 59D. Ages to: RHS 199A.

Flowers:

*Quantity per spadix.*—150 to 170.

*Spadix flower arrangement.*—Bisexual, rounded in cross-section.

*Shape.*—Rounded.

*Size.*—Length: 0.05 cm to 0.1 cm. Diameter (maximum): 0.1 cm.

*Color.*—RHS 63D.

Reproductive organs:

*Stamens.*—Not visible.

*Pollen amount.*—Very few.

*Pollen color.*—RHS 156D.

*Pistil.*—Quantity: Many. Length: Less than 0.01 cm. Color: RHS 156D.

*Style.*—Not observed.

*Stigma.*—Shape: Ovoid. Diameter: Less than 0.01 cm. Color: RHS 63D.

*Ovary.*—Rarely visible.

*Ovary color.*—Not measured.

Fruit and seed set: None observed.

Disease and pest resistance: Not observed to date.

COMPARISON WITH PARENTAL AND COMMERCIAL VARIETIES

'ANTHDATAM' differs from the female parent plant 'ANTHUCOEN' (U.S. Plant Pat. No. 22,630) in that 'ANTHDATAM' has a pink spathe, whereas 'ANTHUCOEN' has a purple spathe.

'ANTHDATAM' differs from male parent plant '10665-03' (unpatented) in that 'ANTHDATAM' has a pink spathe, whereas '10665-03' has a red spathe.

'ANTHDATAM' differs from commercial variety 'Pink Champion' (U.S. Plant Pat. No. 12,115) in that 'ANTHDATAM' has a light green cataphyll and a brown spadix when aged, whereas 'Pink Champion' has a pinkish cataphyll and a green spadix when aged. Additionally, 'ANTHDATAM' has a wider spathe than 'Pink Champion'.

'ANTHDATAM' differs from commercial variety 'ANTHCOPYLI' (unpatented) in that 'ANTHDATAM' has a brown spadix when aged, whereas 'ANTHCOPYLI' has a green spadix when aged. Additionally, 'ANTHDATAM' has a smaller spathe width and length than 'ANTHCOPYLI'.

I claim:

1. A new and distinct variety of *Anthurium* plant named 'ANTHDATAM', substantially as illustrated and described herein.

* * * * *